United States Patent
Takahashi et al.

(10) Patent No.: US 11,124,467 B2
(45) Date of Patent: Sep. 21, 2021

(54) METHOD FOR PRODUCING HYDROCHLOROFLUOROCARBON AND/OR HYDROFLUOROCARBON

(71) Applicant: DAIKIN INDUSTRIES, LTD., Osaka (JP)

(72) Inventors: Kazuhiro Takahashi, Osaka (JP); Shuuzou Kida, Osaka (JP); Tatsuya Takakuwa, Osaka (JP); Masanobu Nishitsuji, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 16/094,256

(22) PCT Filed: Apr. 20, 2017

(86) PCT No.: PCT/JP2017/015945
§ 371 (c)(1),
(2) Date: Oct. 17, 2018

(87) PCT Pub. No.: WO2017/183702
PCT Pub. Date: Oct. 26, 2017

(65) Prior Publication Data
US 2019/0127299 A1     May 2, 2019

(30) Foreign Application Priority Data
Apr. 21, 2016 (JP) .............. JP2016-085289

(51) Int. Cl.
*C07C 17/25* (2006.01)
*C07C 17/20* (2006.01)
(Continued)

(52) U.S. Cl.
CPC ......... *C07C 17/206* (2013.01); *B01J 19/2445* (2013.01); *B01J 23/90* (2013.01);
(Continued)

(58) Field of Classification Search
CPC ...... C07C 17/25; C07C 17/206; C07C 17/087
See application file for complete search history.

(56) References Cited

U.S. PATENT DOCUMENTS

| 2010/0048961 A1 | 2/2010 | Merkel et al. |
| 2012/0065435 A1 | 3/2012 | Nishiguchi et al. |

(Continued)

FOREIGN PATENT DOCUMENTS

| JP | 59-108726 | 6/1984 |
| JP | 2003-286207 | 10/2003 |

(Continued)

OTHER PUBLICATIONS

JP59108726, Jun. 23, 1984, pp. 1-5; English translation (Year: 1984).*

(Continued)

*Primary Examiner* — Medhanit W Bahta
(74) *Attorney, Agent, or Firm* — Wenderoth, Lind & Ponack, L.L.P.

(57) ABSTRACT

Provided is a method for producing HCFC and/or HFC by subjecting a halogenated hydrocarbon and anhydrous hydrogen fluoride to a fluorination reaction in the presence of a catalyst, whereby efficient production can be achieved, without the need to stop the production every time catalytic activity is regenerated or recovered, and without making facilities excessive. Provided as a solution therefor is a method comprising
(A) subjecting a halogenated hydrocarbon and anhydrous hydrogen fluoride to a fluorination reaction in at least two reactors each in the presence of a catalyst to thereby obtain HCFC and/or HFC; and
(B) while halting the reaction in at least one of the reactors, obtaining HCFC and/or HFC by the reaction in at least one other reactor.

13 Claims, 2 Drawing Sheets

(51) Int. Cl.

| | | |
|---|---|---|
| *C07C 17/087* | (2006.01) | |
| *C07C 21/18* | (2006.01) | |
| *C07C 19/08* | (2006.01) | |
| *B01J 23/90* | (2006.01) | |
| *B01J 19/24* | (2006.01) | |
| *C07B 61/00* | (2006.01) | |

(52) U.S. Cl.
CPC ............ *C07C 17/087* (2013.01); *C07C 17/20* (2013.01); *C07C 17/25* (2013.01); *C07C 21/18* (2013.01); *B01J 2219/00033* (2013.01); *C07B 61/00* (2013.01)

(56) References Cited

U.S. PATENT DOCUMENTS

| | | | | |
|---|---|---|---|---|
| 2014/0031597 | A1* | 1/2014 | Deur-Bert | B01J 23/866 570/160 |
| 2017/0210686 | A1* | 7/2017 | Pigamo | B01J 12/007 |
| 2019/0210943 | A1* | 7/2019 | Deur-Bert | C07C 21/18 |
| 2019/0218162 | A1* | 7/2019 | Deur-Bert | B01J 8/0278 |

FOREIGN PATENT DOCUMENTS

| | | | |
|---|---|---|---|
| JP | 2010-47573 | 3/2010 | |
| JP | 2012-82189 | 4/2012 | |
| JP | 2014-511350 | 5/2014 | |
| JP | 2014-511351 | 5/2014 | |
| WO | 03/004445 | 1/2003 | |
| WO | 2007/079431 | 7/2007 | |
| WO | 2012/098421 | 7/2012 | |
| WO | 2012/098422 | 7/2012 | |
| WO | 2013/111911 | 8/2013 | |
| WO | 2013/141409 | 9/2013 | |
| WO | WO-2016001515 A1 * | 1/2016 | ............ B01J 12/007 |

OTHER PUBLICATIONS

WO2016001515—translation, Jan. 2016, pp. 1-31 (Year: 2016).*
International Search Report dated Aug. 1, 2017 in International (PCT) Application No. PCT/JP2017/015945.
Extended European Search Report dated Nov. 18, 2019 in European Patent Application No. 17786039.2.
J. Sattler et al., "Catalytic Dehydrogenation of Light Alkanes on Metals and Metal Oxides", Chemical Reviews, vol. 114, No. 20, Oct. 2014, pp. 10613-10653.

* cited by examiner

METHOD FOR PRODUCING HYDROCHLOROFLUOROCARBON AND/OR HYDROFLUOROCARBON

TECHNICAL FIELD

The present invention relates to a method for producing hydrochlorofluorocarbon and/or hydrofluorocarbon.

BACKGROUND ART

Various hydrochlorofluorocarbons (HCFC) and hydrofluorocarbons (HFC) are used as useful compounds. For example, 2,3,3,3-tetrafluoropropene (HFO-1234yf) represented by the chemical formula: $CF_3CF=CH_2$, which is a hydrofluoroolefin (HFO), has been regarded as a promising refrigerant for car air conditioners etc., because of its low global warming potential (GWP).

As the method for producing HFC, including HFO-1234yf, various methods have been proposed so far, in which a halogenated hydrocarbon, which is used as a raw material compound, and anhydrous hydrogen fluoride are subjected to a vapor-phase fluorination reaction in the presence of a catalyst to thereby obtain HFC. As such a method, for example, PTL 1 and PTL 2 each propose a method for producing 2-chloro-3,3,3-trifluoropropene (HCFO-1233xf) and HFO-1234yf using 1,1,1,2,3-pentachloropropane (HCC-240db) as a raw material compound. Further, PTL 3 discloses a method for producing HFO-1234yf using 1,1,2,3-tetrachloropropene (HCC-1230xa) as a raw material compound.

CITATION LIST

Patent Literature

PTL 1: WO2013/141409
PTL 2: WO2013/111911
PTL 3: WO2007/079431

SUMMARY OF INVENTION

Technical Problem

The present inventors found that the method for obtaining HCFC and/or HFC by subjecting a halogenated hydrocarbon and anhydrous hydrogen fluoride to a fluorination reaction in the presence of a catalyst had problems in that catalytic activity and selectivity were reduced as the reaction time passed, thereby decreasing the productivity.

A possible solution for this problem was to perform the operation of regenerating or recovering the catalyst while completely stopping the reaction process. Specifically, after reactive gas remaining in the reactor is purged, regeneration gas is supplied to regenerate the catalyst; then, after completion of regeneration, the regeneration gas is purged, reactive gas is supplied, and the reactor is started. However, the present inventors clarified that when the reaction process was thus completely stopped, there were other problems in that because it was necessary to stop the production every time the catalyst was regenerated, this made the production significantly inefficient, made facilities excessive, and caused large troubles in the stable operation of the entire process. Further, the present inventors clarified that there was a unique problem in the regeneration using regeneration gas, i.e., loss of reactive gas.

The present invention is intended to solve these problems in the method for obtaining HCFC and/or HFC by subjecting a halogenated hydrocarbon and anhydrous hydrogen fluoride to a vapor-phase fluorination reaction in the presence of a catalyst. Specifically, an object of the present invention is to provide a method that can achieve efficient production, without loss of reactive gas, without the need to stop the production every time catalytic activity is regenerated or recovered, and without making facilities excessive.

Solution to Problem

The present inventors conducted extensive research to solve the above problems, and consequently found that when a catalyst is regenerated or recovered using two or more reactors and a recovering device connected to these reactors by continuing a reaction in at least one of the reactors, while halting the reaction in at least one other reactor, if necessary, the catalyst deteriorated over time can be regenerated or recovered in a timely manner without loss of reactive gas and without stopping the entire process. Thus, the present invention has been completed.

More specifically, the present invention includes the following embodiments.

Item 1. A method for producing hydrochlorofluorocarbon (HCFC) and/or hydrofluorocarbon (HFC), the method comprising:

(A) subjecting a halogenated hydrocarbon to a fluorination reaction using anhydrous hydrogen fluoride in at least two reactors each in the presence of a catalyst to thereby obtain HCFC and/or HFC; and (B) while halting the reaction in at least one of the reactors, obtaining HCFC and/or HFC by the reaction in at least one other reactor.

Item 2. The method according to Item 1, wherein in step (B), catalytic activity is regenerated or recovered in the at least one reactor in which the reaction is halted.

Item 3. The method according to Item 1 or 2, further comprising the following step (C).

(C) collecting the HCFC and/or HFC obtained in step (A) using a recovering device connected to the at least two reactors.

Item 4. The method according to Item 3, wherein in step (C), a composition containing the HFC and/or HFC obtained in step (A) is separated from a composition containing an unreacted halogenated hydrocarbon and/or unreacted anhydrous hydrogen fluoride.

Item 5. The method according to Item 3 or 4, wherein in step (C), the recovering device is at least one recovering device selected from the group consisting of distillation columns, liquid separation devices, and flash columns.

Item 6. The method according to any one of Items 3 to 5, further comprising the following step (D):

(D) recycling the unreacted compounds obtained in step (C) as raw material compounds in the reactors.

Item 7. A method for producing HCFC and/or HFC, the method comprising:

(a) subjecting a halogenated hydrocarbon to a fluorination reaction using anhydrous hydrogen fluoride in at least two reactors each in the presence of a catalyst to thereby obtain HCFC and/or HFC; and (b) collecting the HCFC and/or HFC obtained in step (a) at least using a recovering device connected to the at least two reactors.

Item 8. The method according to Item 7, further comprising the following step (c):

(c) collecting a composition containing an unreacted halogenated hydrocarbon and/or unreacted anhydrous hydrogen fluoride at least using a recovering device connected to the at least two reactors.

Item 9. The method according to Item 8, further comprising the following step (d):

(d) recycling the unreacted compounds obtained in step (c) as raw material compounds in the reactors.

Item 10. The method according to any one of Items 7 to 9, wherein step (a) is the following step (a'):

(a') while halting the reaction in at least one of the reactors, obtaining HCFC and/or HFC by the reaction in at least one other reactor.

Item 11. The method according to Item 10, wherein in step (a'), catalytic activity is regenerated or recovered in the at least one reactor in which the reaction is halted.

Item 12. The method according to any one of Items 1 to 11, wherein HCFC and/or HFC are continuously produced.

Item 13. The method according to any one of Items 1 to 12, wherein the HCFC and HFC contain $C_2$-$C_4$ HCFC and $C_2$-$C_4$ HFC, respectively.

Item 14. The method according to any one of Items 1 to 12, wherein the HFC contains 2,3,3,3-tetrafluoropropene (HFO-1234yf).

Item 15. The method according to any one of items 1 to 14, wherein the halogenated hydrocarbon is a $C_2$-$C_4$ halogenated hydrocarbon that is substituted with at least one chlorine atom and/or fluorine atom, and that may have an unsaturated bond.

Item 16. The method according to any one of Items 1 to 14, wherein the halogenated hydrocarbon is at least one halogenated hydrocarbon selected from the group consisting of a halogenated hydrocarbon represented by the general formula:

$$CH_gCl_hF_{(3-g-h)}CH_iCl_{(2-i)}CH_jCl_{(3-j)};$$

and a halogenated hydrocarbon represented by the general formula:

$$CH_kCl_lF_{(3-k-l)}CH_mCl_{(1-m)}=CH_nCl_{(2-n)}$$

wherein in both formulas, g, k, i, and n are each an integer of 0 to 2; h, j, and l are each an integer of 0 to 3; and each m is 0 or 1.

Item 17. The method according to any one of Items 1 to 14, wherein the halogenated hydrocarbon is at least one halogenated hydrocarbon selected from the group consisting of 1,1,2,2,3-pentachloropropane (HCC-240aa), 1,1,1,2,3-pentachloropropane (HCC-240db), 1,1,1,3,3-pentachloropropane (HCC-240fa), 1,2,3-trichloro-1,1-difluoropropane (HCFC-242dc), 2,3-dichloro-1,1,1-trifluoropropane (HCFC-243db), 1,1,2,3-tetrachloropropene (HCO-1230xa), 2,3,3,3-tetrachloropropene (HCO-1230xf), 2,3-dichloro-3,3-difluoropropene (HCFO-1232xf), 2-chloro-3,3,3-trifluoropropene (HCFO-1233xf), and 1-chloro-3,3,3-trifluoropropene (HCFO-1233zd).

Item 18. The method according to any one of Items 1 to 14, wherein the halogenated hydrocarbon contains HCFO-1233xf.

Item 19. A system used for the method according to any one of Items 1 to 18, the system comprising:

(a) at least two reactors each containing a catalyst suitable for a reaction for obtaining HCFC and/or HFC by a fluorination reaction of a halogenated hydrocarbon using anhydrous hydrogen fluoride; and (b) a recovering device connected to the at least two reactors (a).

Item 20. Use of a system for the method according to any one of Items 1 to 18, the system comprising:

(a) at least two reactors each containing a catalyst suitable for a reaction for obtaining HCFC and/or HFC by a fluorination reaction of a halogenated hydrocarbon using anhydrous hydrogen fluoride; and (b) a recovering device connected to the at least two reactors (a).

Advantageous Effects of Invention

According to the present invention, in a method for producing HCFC and/or HFC by subjecting a halogenated hydrocarbon, which is used as a raw material compound, and anhydrous hydrogen fluoride to a vapor-phase fluorination reaction in the presence of a catalyst, catalytic activity deteriorated over time can be recovered in a timely manner without stopping the entire process and without loss of reactive gas.

DESCRIPTION OF EMBODIMENTS

Figure 1:
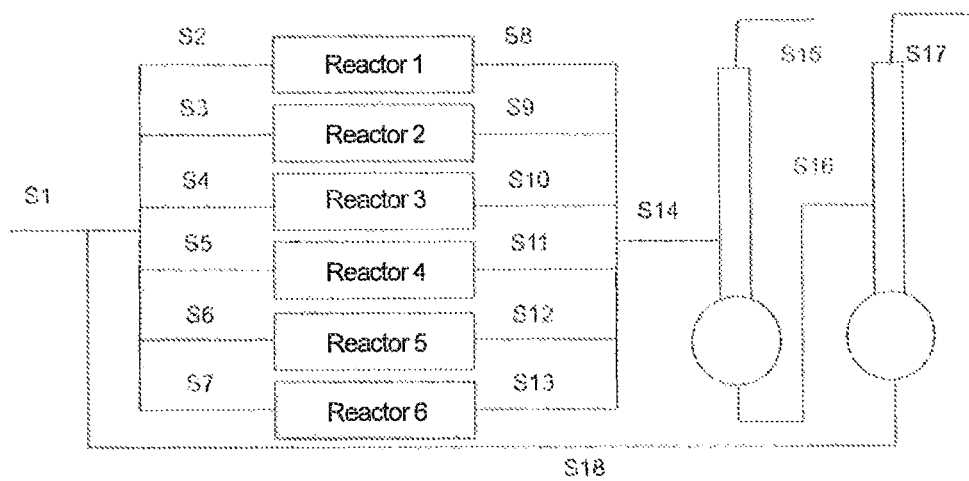
FIG. 1 is a flow chart schematically showing one embodiment of the present invention.

In the present specification, the term "hydrofluorocarbon (HFC)" is used as a term including "hydrofluoroolefin (HFO)."

In the present specification, the term "hydrochlorofluorocarbon (HCFC)" is used as a term including "hydrochlorofluoroolefin (HCFO)."

The following shows compound names represented by abbreviations of many halogenated hydrocarbons used in the present specification, and their structural formulas.

HCC-240 aa
1,1,2,2,3-pentachloropropane
$CHCl_2CCl_2CH_2Cl$
HCC-240db
1,1,1,2,3-pentachloropropane
$CCl_3CHClCH_2Cl$
HCC-240fa
1,1,1,3,3-pentachloropropane
$CCl_3CH_2CHCl_2$
HCFC-242dc
1,2,3-trichloro-1,1-difluoropropane
$CClF_2CHClCH_2Cl$
HCFC-243db
2,3-dichloro-1,1,1-trifluoropropane
$CF_3CHClCH_2Cl$
HCO-1230xa
1,1,2,3-tetrachloropropene
$CH_2ClCCl=CCl_2$
HCO-1230xf
2,3,3,3-tetrachloropropene
$CCl_3CCl=CH_2$
HCFO-1232xf
2,3-dichloro-3,3-difluoropropene
$CClF_2CCl=CH_2$
HCFO-1233xf
2-chloro-3,3,3-trifluoropropene
$CF_3CCl=CH_2$
HCFO-1233zd
1-chloro-3,3,3-trifluoropropene CF$_3$CH=CHCl The method for producing HCFC and/or HFC according to the present invention is described in detail below.

1. Raw Material Compound

The raw material compound is not particularly limited, and may be a halogenated hydrocarbon that can produce HCFC and/or HFC upon a vapor-phase fluorination reaction with anhydrous hydrogen fluoride.

As the raw material compound, the halogenated hydrocarbons mentioned above can be used singly or in combination of two or more. The raw material compound is generally a halogenated hydrocarbon having the same number of carbon atoms as that of the target HCFC and/or HFC to be produced by the production method of the present invention.

Specific examples of the halogenated hydrocarbon as a raw material compound include C$_2$-C$_5$ halogenated hydrocarbons that are substituted with at least one chlorine atom and/or fluorine atom and that may have an unsaturated bond.

In the above description, the unsaturated bond may be a double bond or a triple bond, but is preferably a double bond.

The C$_2$-C$_5$ halogenated hydrocarbon that is substituted with at least one chlorine atom and/or fluorine atom and that may have an unsaturated bond, as a raw material compound, is preferably a halogenated hydrocarbon having an unsaturated bond at the terminal, and particularly preferably a halogenated hydrocarbon having a double bond at the terminal.

In the C$_2$-C$_5$ halogenated hydrocarbon that is substituted with at least one chlorine atom and/or fluorine atom and that may have an unsaturated bond, the number of carbon atoms is preferably 2 to 4, and more preferably 3.

More specific examples of C$_3$ halogenated hydrocarbons mentioned above include halogenated hydrocarbons represented by Formula (1):

$$CH_gCl_hF_{(3-g-h)}CH_iCl_{(2-i)}CH_jCl_{(3-j)};$$

or Formula (2):

$$CH_kCl_hF_{(3-k-l)}CH_mCl_{(1-m)}=CH_nCl_{(2-n)}$$

wherein in both formulas, g, k, i, and n are each an integer of 0 to 2; h, j, and l are each an integer of 0 to 3; and each m is 0 or i.

The C$_3$ halogenated hydrocarbon represented by Formula (1) is preferably a halogenated hydrocarbon represented by Formula (1a):

$$CH_gCl_hF_{(3-g-h)}CH_iCl_{(2-i)}CH_2Cl$$

wherein each symbol is as defined above.

Preferable examples of the C$_3$ halogenated hydrocarbon used as a raw material compound include 1,1,2,2,3-pentachloropropane (HCC-240aa), 1,1,1,2,3-pentachloropropane (HCC-240db), 1,1,1,3,3-pentachloropropane (HCC-240fa), 1,2,3-trichloro-1,1-difluoropropane (HCFC-242dc), 2,3-dichloro-1,1,1-trifluoropropane (HCFC-243db), 1,1,2,3-tetrachloropropene (HCO-1230xa), 2,3,3,3-tetrachloropropene (HCO-1230xf), 2,3-dichloro-3,3-difluoropropene (HCFO-1232xf), 2-chloro-3,3,3-trifluoropropene (HCFO-1233xf), and 1-chloro-3,3,3-trifluoropropene (HCFO-1233zd).

Of these raw material compounds, particularly HCC-240db, HCO-1230xf, and HCO-1230xa are advantageous in that they are easily available and inexpensive.

The target HCFC and/or HFC to be produced by the production method of the present invention are not particularly limited. Examples of products obtained using a C$_3$ halogenated hydrocarbon as a raw material compound include HCFC and/or HFC represented by Formula (3):

$$CF_3CH_pCl_qF_{(2-p-q)}CH_rCl_sF_{(3-r-s)};$$

or Formula (4):

$$CF_3CH_tCl_uF_{(1-t-u)}=CH_vCl_wF_{(2-v-w)}$$

wherein in both formulas, p, q, v, and w are each an integer of 0 to 2, provided that their total does not exceed 2; r and s are each an integer of 0 to 3, provided that their total does not exceed 3; and t and u are each an integer of 0 or 1, provided that their total does not exceed 1.

The target HCFC and/or HFC to be produced by the production method of the present invention are not particularly limited; however, examples include HFO-1234yf, which is regarded as promising refrigerants for car air conditioners etc., and foaming agents, heat media, aerosol propellants, solvents, etc., due to its low global warming potential (GWP). Other examples include HFO-1234ze and HFO-1243zf (isomers of HFO-1234yf) and production intermediates thereof, which are regarded as promising refrigerants, foaming agents, heat media, aerosol propellants, solvents, etc. Still other examples include HCFO-1233zd and HCFO-1233xf, which are regarded as promising refrigerants, foaming agents, heat media, solvents, etc.

When the target HCFC and/or HFC produced by the production method of the present invention are HFO-1234yf, it is preferable to use at least HCFO-1233xf as a raw material compound, although it is not particularly limited thereto.

2. Vapor-Phase Fluorination Reaction

In the present invention, the above-mentioned raw material compound can be reacted with anhydrous hydrogen fluoride in a vapor phase in the presence of a catalyst.

It is sufficient that the raw material compound and anhydrous hydrogen fluoride each in a gaseous state can be brought into contact with each other in the presence of a catalyst. The raw material compound may be in a liquid state when supplied into a reactor.

3. Liquid-Phase Fluorination Reaction

In the present invention, the raw material compound mentioned above can also be reacted with anhydrous hydrogen fluoride in a liquid phase in the presence of a catalyst (also referred to as a fluorinating agent).

In this case, anhydrous hydrogen fluoride and the raw material compound can be reacted in a liquid-phase reactor in the presence of at least one catalyst selected from the group consisting of SbCl$_5$, TaCl$_5$, NbCl$_5$, SnCl$_4$, TiCl$_4$, MoCl$_5$, FeCl$_3$, and halides obtained by replacing some or all of the chlorine atoms of these with fluorine atoms.

The reaction can be continuously performed by continuously extracting products to the outside of the reaction system, and adding raw materials. The halides mentioned above lose their activity when the valence is reduced to form SbCl$_3$ etc. during reaction; thus, it is preferable to regenerate the catalyst using an oxidizing substance, such as chlorine, to return the valence to the original valence.

The method for vaporizing the raw material compound in a reaction region is not particularly limited. For example, a vaporizing device comprising a reaction tube filled with a material that has excellent thermal conductivity and no catalytic activity for the reaction of the present invention, and that is stable against anhydrous hydrogen fluoride, can be used. For example, when the raw material compound is liquid at ordinary temperature and ordinary pressure, the raw material compound is vaporized by a vaporizer, then allowed to pass through a preheating region, and supplied in a mixing region in which it is brought into contact with anhydrous hydrogen fluoride, and the mixture is mixed therein. Then, temperature distribution is made uniform, and the mixture is supplied in a reactor filled with a catalyst; thus, the reaction can be performed in a vapor-phase state.

Moreover, as the method for supplying the raw material compound into the reactor, for example, anhydrous hydrogen fluoride is heated to a temperature equal to or higher than the vaporization temperature of the raw material compound, and then supplied, together with the raw material compound in a liquid state, to a device for vaporization and mixing, so that the raw material compound is vaporized and supplied in a vapor-phase state to the reactor.

In the above description, the materials having excellent thermal conductivity are not particularly limited; for example, metal pieces of corrosion-resistant materials, such as nickel beads, alumina beads, Hastelloy, Inconel, Monel, or Incoloy, can be used.

Anhydrous hydrogen fluoride may generally be supplied in a vapor-phase state, together with the raw material compound, to the reactor. The amount of anhydrous hydrogen fluoride supplied is generally such that the total molar ratio of halogenated hydrocarbon as a raw material compound to anhydrous hydrogen fluoride is preferably 10 or more, in order to suppress the deterioration of catalytic activity. The upper limit of the molar ratio can be adjusted to an optimal value so as to be advantageous in energy efficiency. In this respect, the molar ratio is preferably 100 or less, and more preferably 50 or less.

In the above description, in order to suppress the deterioration of catalytic activity, the amount of anhydrous hydrogen fluoride is more preferably such that the total molar ratio of halogenated hydrocarbon is 4 or more, and even more preferably 8 or more.

The raw material compound and/or anhydrous hydrogen fluoride may be supplied to the reactor as it is, or may be supplied after dilution with an inert gas, such as nitrogen, helium, or argon. Further, in order to suppress the deterioration of catalytic activity, at least one oxidative gas, such as fluorine, oxygen, or chlorine, may be added.

In order to maintain catalytic activity for a long period of time, the above raw material may be supplied, together with oxygen, to the reactor. In this case, the amount of oxygen supplied may be about 0.01 to 0.3 mol per mol of halogenated hydrocarbon, which is a raw material compound, based on the amount of halogenated hydrocarbon supplied.

As a fluorination catalyst, a known catalyst having activity against a fluorination reaction using hydrogen fluoride can be used. Usable examples include metal oxides and fluorinated metal oxides, such as chromium oxide, fluorinated chromium oxide, aluminum fluoride, and fluorinated aluminum oxide. In addition, metal fluorides, such as $MgF_2$, $TaF_5$, and $SbF_5$, can also be used.

Among these catalysts, it is preferable to use, for example, chromium oxide represented by the composition formula: $CrO_m$, wherein m is in the range of $1.5<m<3$, more preferably in the range of $2<m<2.75$, and even more preferably in the range of $2<m<2.3$, although it is not particularly limited thereto. The chromium oxide catalyst may be any shape, such as powder or pellets, as long as it is suitable for the reaction. A pellet shape is particularly preferable. The chromium oxide catalyst mentioned above can be prepared, for example, by the method disclosed in JPH05-146680A.

Moreover, fluorinated chromium oxide can be prepared by the method disclosed in JPH05-146680A. For example, the fluorinated chromium oxide can be obtained by fluorination (HF treatment) of chromium oxide obtained by the above method with hydrogen fluoride.

Although the degree of fluorination is not particularly limited, for example, those having a fluorine content of about 10 to 45 wt % can be suitably used.

Further, the chromium catalyst disclosed in JPH11-171806A, which comprises, as a main component, a chromium compound containing at least one metal element selected from the group consisting of indium, gallium, cobalt, nickel, zinc, and aluminum, wherein the average valence number of chromium in the chromium compound is +3.5 or more and +5.0 or less, and the chromium catalyst is in an amorphous state, can also be used as a chromium oxide catalyst or a fluorinated chromium oxide catalyst.

The above fluorination catalyst can be used after being carried on a carrier, such as alumina or activated carbon.

The form of the reactor is not particularly limited. For example, an adiabatic reactor packed with a catalyst, a multi-tube reactor cooled using a heat medium, or the like can be used.

The reactor used is preferably a reactor comprising an alloy containing 30 wt % or more of nickel. Specifically, reactors comprising materials having resistance to the corrosive action of hydrogen fluoride, such as Hastelloy, Inconel, Monel, and Incoloy, are preferably used.

As the reaction temperature, the temperature in the reactor is suitably about 200 to 500° C., and preferably about 250 to 450° C.; however, because optimal temperature conditions vary depending on each reaction, a temperature optimal in terms of substance yield is selected within the above temperature range. The selectivity of HFO is improved when the temperature is equal to or less than the upper limit of this temperature range, and the conversion of the raw material compound is improved when the temperature is equal to or more than the lower limit of this temperature range.

The pressure during reaction is not particularly limited, and the reaction can be performed under ordinary pressure or increased pressure. That is, the reaction in the present invention can be performed under atmospheric pressure (0.1 MPa), and may be performed under increased pressure up to about 1.0 MPa.

Although the reaction time is not particularly limited, the contact time represented by W/Fo, which is the ratio of the amount of catalyst W (g) to the total flow (total amount of the raw material compound and anhydrous hydrogen fluoride) Fo (flow rate at 0° C. and 1 atm: cc/sec) of the raw material gases supplied to the reactor, may generally be in the range of about 5 to 20 g-sec/cc.

4. Product Composition

According to the vapor-phase fluorination reaction described above, a composition containing HCFC and/or HFC, which are target compounds, can be obtained as a product composition. Specifically, the product composition can be obtained at the outlet of the reactor. HCFC and/or HFC can be collected from the obtained product composition by purification by distillation, adsorption, membrane separation, or like method.

The method for producing HCFC and/or HFC according to the present invention is particularly useful as a method for producing hydrofluoroolefin (HFO). Accordingly, the product composition of the present invention is particularly preferably a composition containing HFO.

The product composition generally contains by-products, including HCl, as reaction products, in addition to HCFC and/or HFC, which are target compounds. Further, the product composition contains the unreacted raw material compound, anhydrous hydrogen fluoride, etc.

In the present specification, various compounds contained in the product composition are classified into the following groups.

The main product composition is a composition mainly containing HCFC and/or HFC, which are target compounds.

The unreacted composition is a composition mainly containing the raw material compound and anhydrous hydrogen fluoride. In the present specification, the term "unreacted composition" means a composition mainly containing the raw material compound and anhydrous hydrogen fluoride; however, at least part of the raw material compound contained therein may be a reaction by-product, regardless of its origin, as long as it is the same as the raw material compound as a substance.

The by-product composition is a composition mainly containing by-products.

These compositions can be separated by operation, such as distillation and/or liquid separation.

In the present specification, the term "distillation" includes flash distillation. The phrase "mainly contain" represents a concept reflecting purity that can be achieved by general separation operation. In general, the total amount of other components is 10 mol % or less, preferably 5 mol % or less, and more preferably 2 mol % or less, based on the entire composition.

For example, when HCFO-1233xf is used as a raw material compound, HFO-1234yf is obtained as HFC, and a relatively small amount of 1,3,3,3-tetrafluoropropene (HFO-1234ze) can also be obtained. In this case, HCl, 1,1,1,2,2-pentafluoropropane (HFC-245cb), HCFO-1233zd, etc., are obtained as by-products.

The thus-obtained product compositions can be separated by means of distillation and/or liquid separation into the following groups:
(a) a main product composition containing HCFC and/or HFC;
(b) a composition containing the unreacted halogenated hydrocarbon and anhydrous hydrogen fluoride; and
(c) a composition containing other by-products.

In the above description, the composition (b) may further contain at least one by-product, which is not limited to the unreacted materials.

Moreover, the above product composition can also be separated by means of distillation and/or liquid separation into the following groups:
(a) a main product composition containing HCFC and/or HFC;
(b1) an unreacted composition containing the unreacted halogenated hydrocarbon and anhydrous hydrogen fluoride; and
(c1) a by-product composition.

In the above description, the unreacted composition refers to a composition mainly containing the raw material compound and anhydrous hydrogen fluoride, and the by-product composition refers to a composition mainly containing by-products, as described above.

As the main product composition, a composition containing one type of HCFC or HFC may be separated, or a composition containing two or more types of HCFC and/or HFC may be separated, if necessary. In a case where two or more types of HCFC and/or HFC are produced, when the target HCFC or HFC is only one type of them, the other type of HCFC and/or HFC is handled as by-products, and may be contained in one or more of the main product composition, the by-product composition, and the unreacted composition. Preferably, HCFC and/or HFC as by-products are handled as the by-product composition when they are produced in large amounts, and may be contained in the main product composition and/or the unreacted composition when they are produced in small amounts.

Alternatively, (b2) an unreacted composition containing one unreacted halogenated hydrocarbon and anhydrous hydrogen fluoride can also be separated by means of distillation and/or liquid separation. Due to the separating means, such as distillation and/or liquid separation, the total proportion of halogenated hydrocarbon and anhydrous hydrogen fluoride in the unreacted composition (b2) is relatively high. The unreacted composition (b2) generally contains other components in a total amount of 10 mol % or less, preferably 5 mol % or less, and more preferably 2 mol % or less, based on the entire composition.

Each of the compositions collected in this manner can be recycled by supplying them again in the reactor, if necessary.

HFO as a target compound can be purified from the composition (a) further through a crude step and a purification step, if necessary. The specific methods of the crude step and the purification step are not particularly limited, and generally used methods can be used widely. For example, water washing, dehydration (drying), distillation, liquid separation, and like means can be used.

5. Partial Reaction Halting Step

One embodiment of the present invention comprises a step of obtaining HCFC and/or HFC by, while halting the reaction in at least one reactor, activating the other reactor(s).

Moreover, another embodiment of the present invention comprises a step of collecting the HCFC and/or HFC obtained by a vapor-phase fluorination reaction, at least using a recovering device connected to at least two reactors. Thereby, while the reaction is halted in at least one reactor, the other reactor(s) can be activated, as in the above embodiment.

In any embodiment, catalytic activity can be regenerated or recovered in the reactor in which the reaction is halted. Thus, catalytic activity can be regenerated or recovered, if necessary, in some of the reactors without stopping the entire process of producing HCFC and/or HFC.

In the above description, the recovering device is not particularly limited, and can be selected widely. For example, a distillation column, a liquid separation device, a flash column, or the like can be used. Among these, a single recovering device may be used, or two or more recovering devices may be used. Moreover, a plurality of the same recovering devices may be used.

In an embodiment using three or more (n number of) reactors, for example, the activated reactors are sequentially alternated so as to maintain a state where x number of reactors are activated, and the reaction is halted in (n-x) number of reactors (this state is expressed as "activated x:halted n-x"). In the above description, n and x are both integers, and x is smaller than n.

Examples of the partial reaction halting step in an embodiment using four reactors include the following (1) and (2):

(1) One reactor is activated, while the reaction is halted in three reactors (activated 1:halted 3). The activated reactors are sequentially alternated while maintaining the state "activated 1:halted 3."

(2) Three reactors are activated, while the reaction is halted in one reactor (activated 3:halted 1). The reactors in which the reaction is halted are sequentially alternated while maintaining the state "activated 3:halted 1."

Examples of the partial reaction halting step in an embodiment using 6 reactors include the following (3):

(3) Three reactors are activated, while catalytic activity is halted in three reactors (activated 3:halted 3). The advantage of this embodiment is that even if one reactor is in an unusable state due to breakdown etc., it is not necessary to stop the entire process when using the remaining two reactors.

Regeneration or recovery of catalytic activity is not particularly limited, and can be performed, for example, in the following manner.

The productive capacity of the reactor in which the reaction is halted can be recovered by regenerating the catalyst by adjusting the temperature of the reactor to a suitable temperature, and supplying gas (also referred to as "regeneration gas") obtained by diluting oxidative gas with suitable balance gas; alternatively, the productive capacity of the reactor can be recovered by exchanging or refilling the catalyst. In general, catalysts are deteriorated as they are used so that their activity is not recovered by regeneration operation, or productivity may be reduced because the flow of gas gets worse due to the deposition of corrosives etc. In such a case, the catalyst may be exchanged, refilled, or the like, if necessary.

The oxidative gas is not particularly limited; for example, fluorine, oxygen, chlorine, etc., are used. The oxidative gases may be used singly or in combination of two or more.

The balance gas is not particularly limited; for example, helium, nitrogen, hydrogen, argon, hydrogen fluoride, hydrogen chloride, etc., are used. The balance gases may be used singly or in combination of two or more.

The regeneration gas used for regeneration can be reused after the recovered regeneration gas is combusted, and generated impurities, such as carbon monoxide and/or carbon dioxide, are removed.

Moreover, catalytic activity can also be recovered by exchanging the catalyst, refilling the catalyst, or the like.

6. System

The system used for the method for producing HCFC and/or HFC of the present invention comprises:

(a) at least two reactors each containing a catalyst suitable for a reaction for obtaining HCFC and/or HFC by a fluorination reaction of a halogenated hydrocarbon and anhydrous hydrogen fluoride; and (b) a recovering device connected to the at least two reactors (a).

The system of the present invention is characterized in that two reactors are connected in parallel to one recovering device. Catalytic activity can thereby be regenerated or recovered, if necessary, in some of the reactors, without stopping the entire process of producing HCFC and/or HFC, as described above.

The number of reactors is not particularly limited, and can be suitably determined depending on the flow rate, and the size, thickness, etc., of each reactor. In one embodiment, when an integer n can be set as the number of reactors considered to be suitable in the light of the above factors, the system may comprise n number of reactors, or may comprise n+1 number of reactors in total, provided that one reactor is regarded as a spare. The system may further comprise two or more reactors as spares.

The system of the present invention can exhibit the above effects as long as it comprises at least one recovering device. Although it is not particularly limited thereto, the system may comprise a plurality of recovering devices. In this case, the recovering devices may be connected to each other in series or in parallel, or some recovering devices may be connected to each other in series while the other recovering devices may be connected to each other in parallel.

EXAMPLES

The present invention is described in more detail below with reference to Examples; however, the present invention is not limited to these Examples.

Example 1

A vapor-phase fluorination process of HCFO-1233xf was performed using anhydrous hydrogen fluoride. The reaction temperature was 365° C., the reaction pressure was 0.5 MPaG, the contact time $W/F_o=20$ ($F_o$ is a feed flow rate at 0° C. and 0.1013 MPa), and the molar ratio of HF and HCFO-1233xf was 10. As a result of this operation, 100 kg/month of HFO-1234yf can be obtained in this process.

The Figure shows the process using 6 reactors. Symbols, such as "S1", are the names of streams.

Tables 1 to 3 show the flow rate (mol/h) of each stream in the process of Example 1.

TABLE 1

|  | S1 | S2 | S3 | S4 | S5 | S6 | S7 |
|---|---|---|---|---|---|---|---|
| HF | 0.87 | 0.174 | 0.174 | 0.174 | 0.174 | 0.174 | 0 |
| HCl | 0 | 0 | 0 | 0 | 0 | 0 | 0 |
| 1233xf | 1.2 | 0.532 | 0.532 | 0.532 | 0.532 | 0.532 | 0 |
| 1234yf | 0 | 0 | 0 | 0 | 0 | 0 | 0 |
| 245cb | 0 | 0 | 0 | 0 | 0 | 0 | 0 |
| 1233zd | 0 | 0 | 0 | 0 | 0 | 0 | 0 |
| E-1234ze | 0 | 0 | 0 | 0 | 0 | 0 | 0 |

TABLE 2

|  | S8 | S9 | S10 | S11 | S12 | S13 | S14 |
|---|---|---|---|---|---|---|---|
| HF | 6.2 | 6.2 | 6.2 | 6.2 | 6.2 | 0 | 31.0 |
| HCl | 0.174 | 0.174 | 0.174 | 0.174 | 0.174 | 0 | 0.87 |
| 1233xf | 0.292 | 0.292 | 0.292 | 0.292 | 0.292 | 0 | 1.46 |
| 1234yf | 0.24 | 0.24 | 0.24 | 0.24 | 0.24 | 0 | 1.20 |
| 245cb | 0.098 | 0.098 | 0.098 | 0.098 | 0.098 | 0 | 0.49 |
| 1233zd | 0.003 | 0.003 | 0.003 | 0.003 | 0.003 | 0 | 0.015 |
| E-1234ze | 0.0034 | 0.0034 | 0.0034 | 0.0034 | 0.0034 | 0 | 0.017 |

TABLE 3

|  | S15 | S16 | S17 | S18 |
|---|---|---|---|---|
| HF | 0 | 31.0 | 0 | 31.0 |
| HCl | 0.87 | 0 | 0 | 0 |
| 1233xf | 0 | 1.46 | 0 | 1.46 |
| 1234yf | 0 | 1.20 | 1.20 | 0 |
| 245cb | 0 | 0.49 | 0 | 0.49 |
| 1233zd | 0 | 0.015 | 0 | 0.015 |
| E-1234ze | 0 | 0.017 | 0 | 0.017 |

Figure 2:
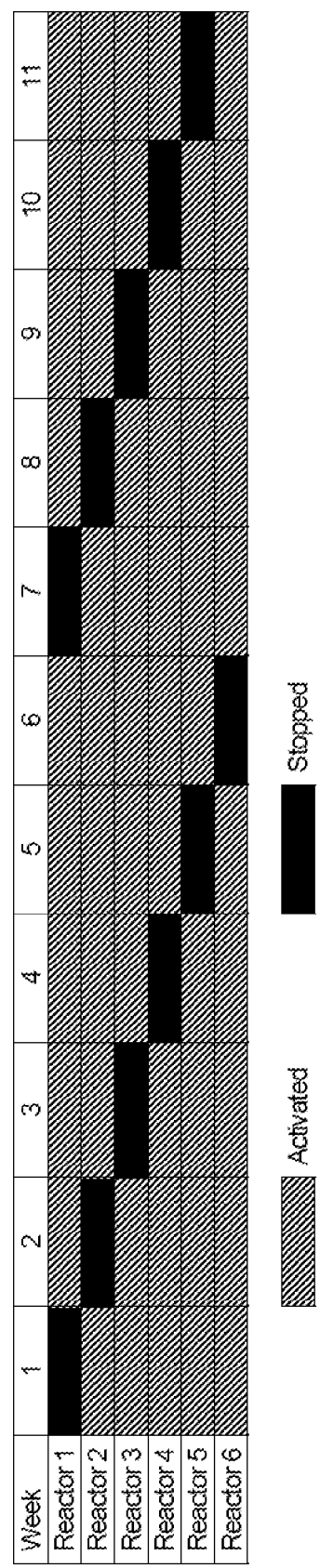
FIG. 2 shows examples of the operating patterns of the reactors of the present invention.

Moreover, FIG. 2 shows examples of the operating patterns of the reactors.

Example 2

The raw material used in the reaction was HCC-240db, the reaction temperature was 280° C., the contact time W/Fo=10 (Fo is a feed flow rate at 0° C. and 0.1013 MPa), and the molar ratio of HF and HCC-240db was 30. Other reaction conditions are the same as those of Example 1. As a result of this operation, 110 kg/month of HFO-1233xf can be obtained in this process.

Tables 5 to 7 show the flow rate (mol/h) of each stream in the process of Example 2.

TABLE 5

|       | S1  | S2     | S3     | S4     | S5     | S6     | S7 |
|-------|-----|--------|--------|--------|--------|--------|----|
| HF    | 3.6 | 7.2    | 7.2    | 7.2    | 7.2    | 7.2    | 0  |
| HCl   | 0   | 0      | 0      | 0      | 0      | 0      | 0  |
| 1233xf| 0   | 0      | 0      | 0      | 0      | 0      | 0  |
| 1232xf| 0   | 0.0024 | 0.0024 | 0.0024 | 0.0024 | 0.0024 | 0  |
| 240db | 1.2 | 0.24   | 0.24   | 0.24   | 0.24   | 0.24   | 0  |

TABLE 6

|       | S8     | S9     | S10    | S11    | S12    | S13 | S14   |
|-------|--------|--------|--------|--------|--------|-----|-------|
| HF    | 6.48   | 6.48   | 6.48   | 6.48   | 6.48   | 0   | 32.4  |
| HCl   | 0.96   | 0.96   | 0.96   | 0.96   | 0.96   | 0   | 4.8   |
| 1233xf| 0.24   | 0.2    | 0.24   | 0.24   | 0.24   | 0   | 1.2   |
| 1232xf| 0.0024 | 0.0024 | 0.0024 | 0.0024 | 0.0024 | 0   | 0.012 |
| 240db | 0      | 0      | 0      | 0      | 0      | 0   | 0     |

TABLE 7

|       | S15 | S16   | S17 | S18   |
|-------|-----|-------|-----|-------|
| HF    | 0   | 32.4  | 0   | 32.4  |
| HCl   | 4.8 | 0     | 0   | 0     |
| 1233xf| 0   | 1.2   | 1.2 | 0     |
| 1232xf| 0   | 0.012 | 0   | 0.012 |
| 240db | 0   | 0     | 0   | 0     |

Example 3

The raw material used in the reaction was HCO-1230xa, the reaction temperature was 280° C., the contact time W/Fo=10 (Fo is a feed flow rate at 0° C. and 0.1013 MPa), and the molar ratio of HF and HCFO-1233xf was 30. Other reaction conditions are the same as those of Example 1. As a result of this operation, 110 kg/month of HFO-1233xf can be obtained in this process.

Tables 8 to 10 show the flow rate (mol/h) of each stream in the process of Example 3.

TABLE 8

|        | S1  | S2    | S3    | S4    | S5    | S6    | S7 |
|--------|-----|-------|-------|-------|-------|-------|----|
| HF     | 3.6 | 7.2   | 7.2   | 7.2   | 7.2   | 7.2   | 0  |
| HCl    | 0   | 0     | 0     | 0     | 0     | 0     | 0  |
| 1233xf | 0   | 0     | 0     | 0     | 0     | 0     | 0  |
| 1232xf | 0   | 0.002 | 0.002 | 0.002 | 0.002 | 0.002 | 0  |
| 1230xa | 1.2 | 0.24  | 0.24  | 0.24  | 0.24  | 0.24  | 0  |

TABLE 9

|        | S8    | S9    | S10   | S11   | S12   | S13 | S14  |
|--------|-------|-------|-------|-------|-------|-----|------|
| HF     | 6.48  | 6.48  | 6.48  | 6.48  | 6.48  | 0   | 32.4 |
| HCl    | 0.96  | 0.96  | 0.96  | 0.96  | 0.96  | 0   | 4.8  |
| 1233xf | 0.24  | 0.24  | 0.24  | 0.24  | 0.24  | 0   | 1.2  |
| 1232xf | 0.002 | 0.002 | 0.002 | 0.002 | 0.002 | 0   | 0.01 |
| 1230xa | 0     | 0     | 0     | 0     | 0     | 0   | 0    |

TABLE 10

|        | S15 | S16  | S17 | S18  |
|--------|-----|------|-----|------|
| HF     | 0   | 32.4 | 0   | 32.4 |
| HCl    | 4.8 | 0    | 0   | 0    |
| 1233xf | 0   | 1.2  | 1.2 | 0    |
| 1232xf | 0   | 0.01 | 0   | 0.01 |
| 1230xa | 0   | 0    | 0   | 0    |

The invention claimed is:

1. A method for producing hydrochlorofluorocarbon (HCFC) and/or hydrofluorocarbon (HFC), the method comprising:
   (A) subjecting at least one halogenated hydrocarbon to a fluorination reaction using anhydrous hydrogen fluoride in at least three reactors each in the presence of a catalyst to thereby obtain HCFC and/or HFC; and
   (B) while halting the reaction in at least one of the reactors, obtaining HCFC and/or HFC by the reaction in at least one other of the reactors which is in an activated state,
   wherein reactors in the activated state are sequentially alternated to as to maintain a state where x number of reactors are activated, and the reaction is halted in (n-x) number of reactors, wherein n and x are both integers, n is a total number of reactors, and x is 2 or more but smaller than n.

2. The method according to claim 1, wherein in step (B), catalytic activity is regenerated or recovered in the at least one reactor in which the reaction is halted.

3. The method according to claim 1, further comprising the following step (C):
   (C) collecting the HCFC and/or HFC obtained in step (A) using a recovering device connected to the at least three reactors.

4. The method according to claim 3, wherein in step (C), a composition containing the HCFC and/or HFC obtained in step (A) is separated from a composition containing an unreacted halogenated hydrocarbon and/or unreacted anhydrous hydrogen fluoride.

5. The method according to claim 3, wherein in step (C), the recovering device is at least one recovering device selected from the group consisting of distillation columns, liquid separation devices, and flash columns.

6. The method according to claim 3, further comprising the following step (D):

(D) recycling the unreacted compounds obtained in step (C) as raw material compounds in the reactors.

7. The method according to claim 1, wherein HCFC and/or HFC are continuously produced.

8. The method according to claim 1, wherein the HCFC and HFC contain $C_2$-$C_4$ HCFC and $C_2$-$C_4$ HFC, respectively.

9. The method according to claim 1, wherein the HFC contains 2,3,3,3-tetrafluoropropene (HFO-1234yf).

10. The method according to claim 1, wherein the at least one halogenated hydrocarbon is at least one $C_2$-$C_4$ halogenated hydrocarbon that is substituted with at least one chlorine atom and/or fluorine atom, and that may have an unsaturated bond.

11. The method according to claim 1, wherein the at least one halogenated hydrocarbon is selected from the group consisting of a halogenated hydrocarbon represented by the formula:

$$CH_gCl_hF_{(3-g-n)}CH_iCl_{(2-i)}CH_jCl_{(3-j)};$$

and a halogenated hydrocarbon represented by the formula:

$$CH_kCl_lF_{(3-k-l)}CH_mCl_{(l-m)}\!\!=\!\!CH_nCl_{(2-n)}$$

wherein in both formulas, g, k, i, and n are each an integer of 0 to 2; h, j, and l are each an integer of 0 to 3; and each m is 0 or 1.

12. The method according to claim 1, wherein the at least one halogenated hydrocarbon is selected from the group consisting of 1,1,2,2,3-pentachloropropane (HCC-240aa), 1,1,1,2,3-pentachloropropane (HCC-240db), 1,1,1,3,3-pentachloropropane (HCC-240fa), 1,2,3-trichloro-1,1-difluoropropane (HCFC-242dc), 2,3-dichloro-1,1,1-trifluoropropane (HCFC-243db), 1,1,2,3-tetrachloropropene (HCO-1230xa), 2,3,3,3-tetrachloropropene (HCO-1230xf), 2,3-dichloro-3,3-difluoropropene (HCFO-1232xf), 2-chloro-3,3,3-trifluoropropene (HCFO-1233xf), and 1-chloro-3,3,3-trifluoropropene (HCFO-1233zd).

13. The method according to claim 1, wherein the at least one halogenated hydrocarbon contains HCFO-1233xf.

* * * * *